United States Patent [19]

Palfray

[11] Patent Number: 5,004,477
[45] Date of Patent: Apr. 2, 1991

[54] PROSTHESIS FOR LEG AMPUTATION AND A PROCESS FOR ITS MANUFACTURE

[75] Inventor: Michel Palfray, Seurre, France

[73] Assignee: Establissements Proteor, France

[21] Appl. No.: 424,525

[22] Filed: Oct. 20, 1989

[30] Foreign Application Priority Data

Oct. 21, 1988 [FR] France ................. 88 13840

[51] Int. Cl.$^5$ ............................ A61F 2/66; A61F 2/60
[52] U.S. Cl. ...................................... 623/53; 623/27; 623/33
[58] Field of Search ................... 623/27–37, 623/53, 55, 54, 56

[56] References Cited

U.S. PATENT DOCUMENTS

| 2,197,093 | 1/1939 | Campbell | 623/56 |
| 2,207,473 | 7/1940 | Beck. | |
| 2,430,584 | 11/1947 | Roche | 623/54 X |
| 2,464,391 | 3/1949 | Havens. | |
| 2,556,525 | 6/1951 | Drennon. | |
| 3,633,573 | 1/1972 | Lipson. | |
| 3,766,569 | 10/1973 | Orange. | |
| 3,871,779 | 3/1975 | Butler | 623/45 |
| 3,909,855 | 10/1975 | Barredo | 623/27 |
| 4,177,525 | 12/1979 | Arbogast et al. . | |
| 4,302,856 | 12/1981 | May | 623/53 |
| 4,652,266 | 3/1987 | Truesdell | 623/55 |

FOREIGN PATENT DOCUMENTS

| 456941 | 3/1928 | Fed. Rep. of Germany . | |
| 3644612 | 7/1988 | Fed. Rep. of Germany | 623/53 |
| 663891 | 8/1929 | France . | |
| 779664 | 4/1935 | France . | |
| 1162321 | 9/1958 | France . | |
| 1300054 | 9/1961 | France . | |
| 0806026 | 2/1981 | U.S.S.R. | 623/27 |
| 761046 | 11/1956 | United Kingdom . | |
| 1371996 | 10/1974 | United Kingdom | 623/55 |
| 2149309 | 6/1985 | United Kingdom . | |

Primary Examiner—Randall L. Green
Assistant Examiner—David H. Willse
Attorney, Agent, or Firm—Scully, Scott, Murphy & Presser

[57] ABSTRACT

The invention relates to a prosthesis for amputation of the leg.

This prosthesis comprises, in monobloc form:
  a socket (1) of a thermosettable resin, preferably provided with reinforcement fibers;
  a hollow leg element (2) rigidly integral with the socket, likewise of a thermosettable resin, preferably provided with reinforcement fibers;
  a hollow foot part (3) rigidly integral with the leg element (2), and in which is lodged a rigid core (26) of a foam of plastic material or similar, this foot part being likewise of a thermosettable material, preferably provided with reinforcement fibers;
  a sole element (4) of a thermosettable resin, preferably provided with reinforcement fibers, closing the hollow foot part at its base.

6 Claims, 2 Drawing Sheets

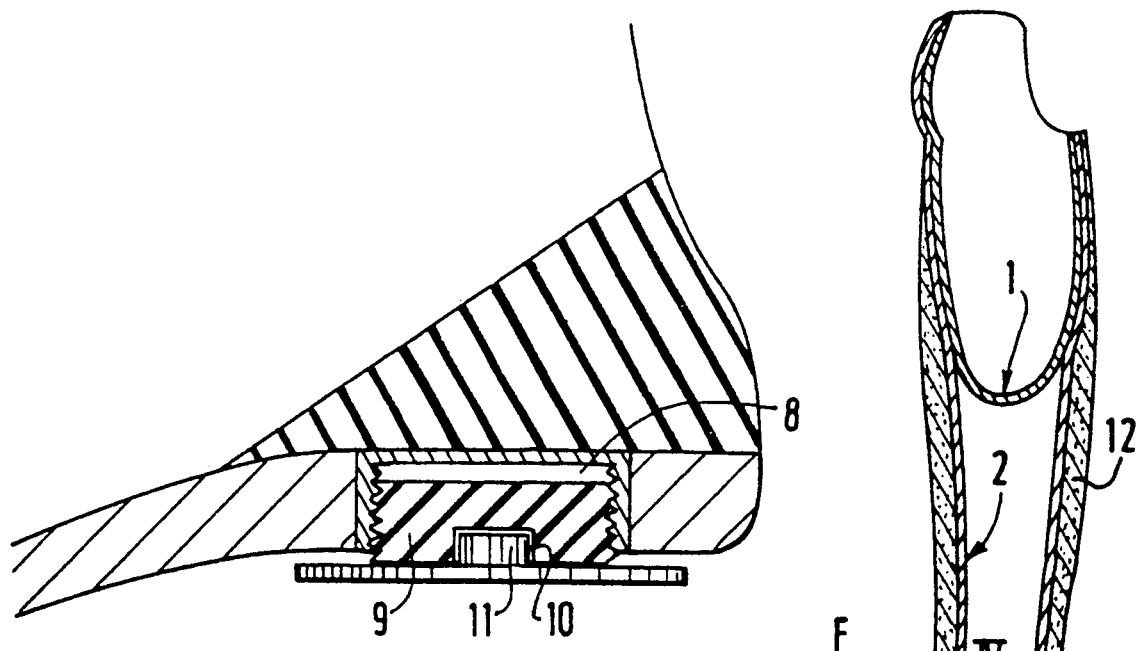
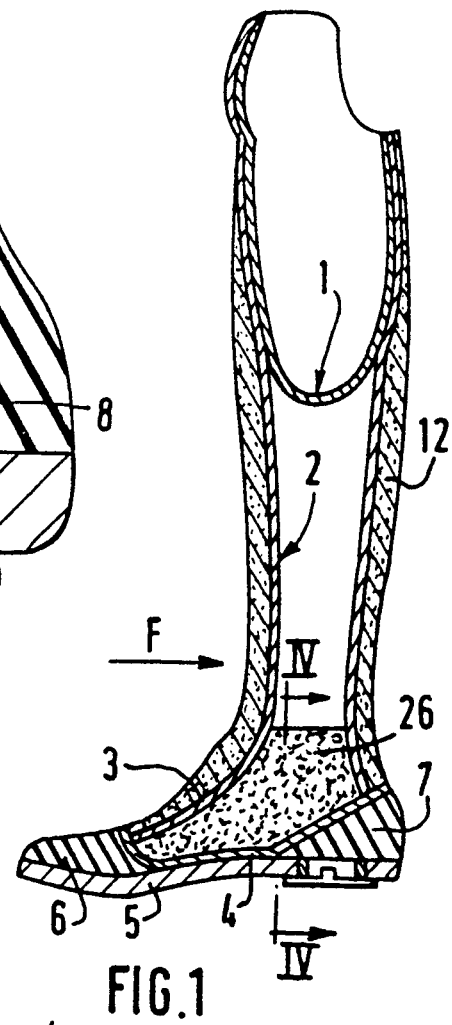
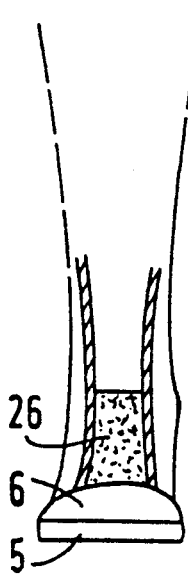
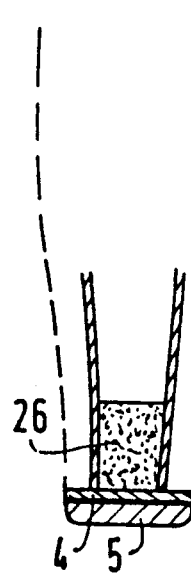
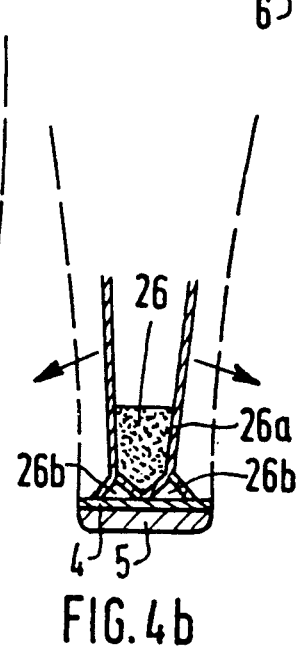
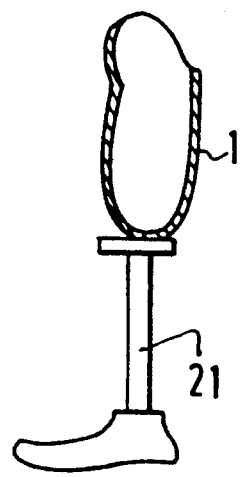

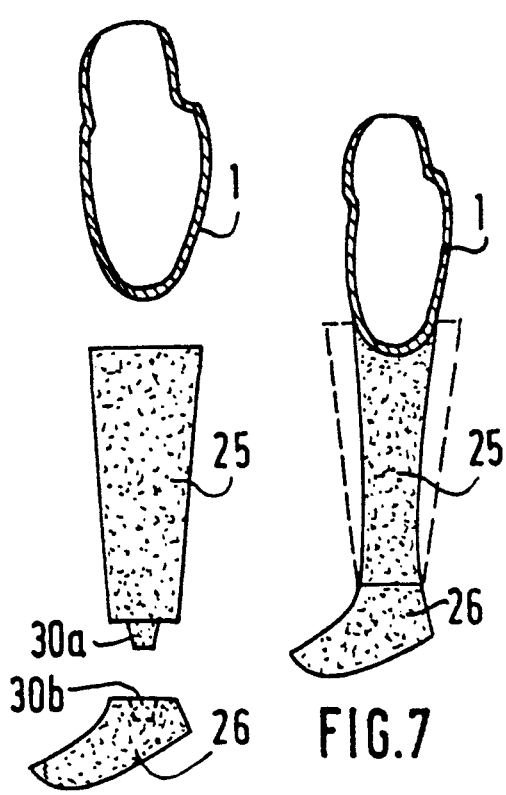
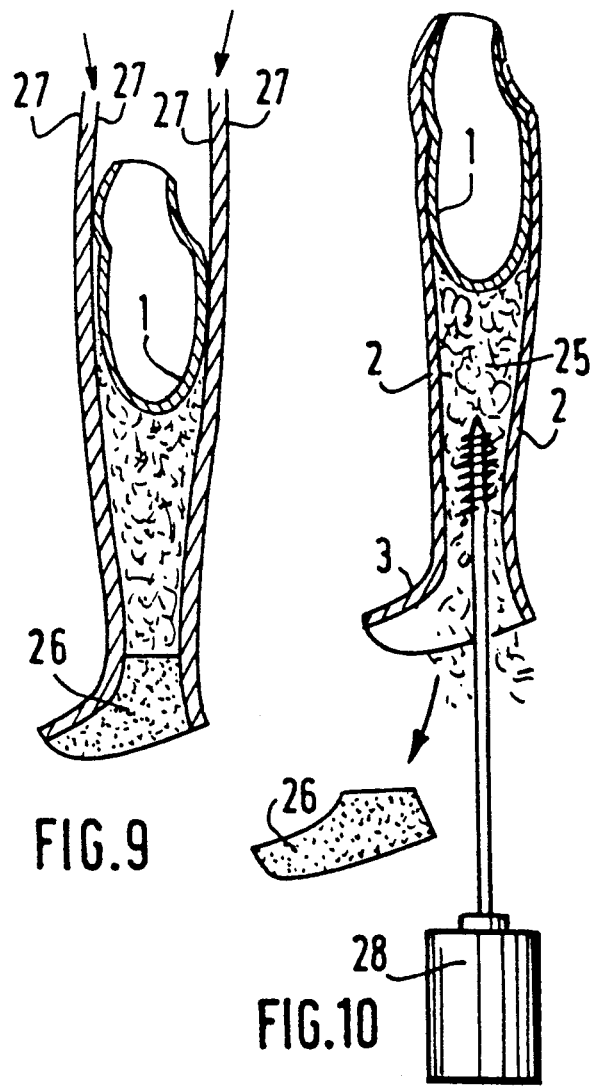
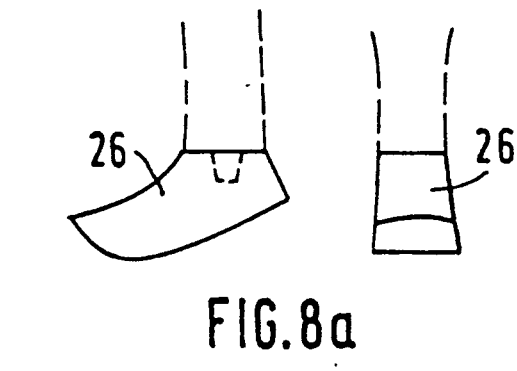
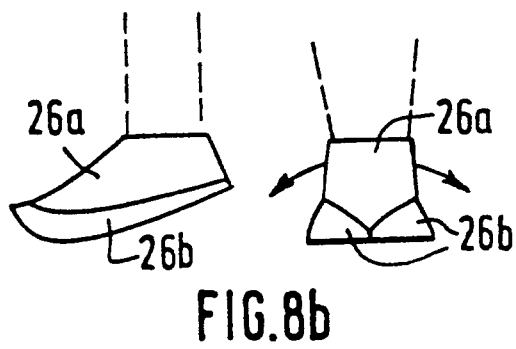
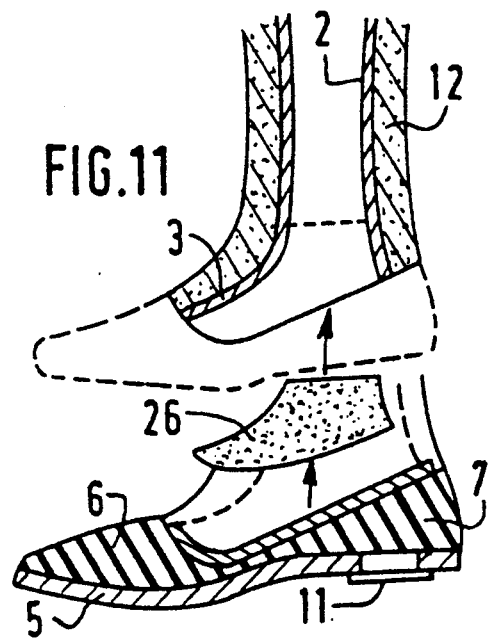

PROSTHESIS FOR LEG AMPUTATION AND A PROCESS FOR ITS MANUFACTURE

BACKGROUND OF THE INVENTION

1. Field of the Invention

The present invention relates to a prosthesis for leg amputation and a process for manufacturing this prosthesis.

It will be remembered that the expression "leg amputation" designates amputations carried out on the lower part of the leg, at the level of the tibia.

The prostheses which are used after such amputations are endoskeletal prostheses, that is to say in which the stump is lodged inside the prosthesis.

2. Discussion of the Prior Art

In the prior art, such prostheses were of aluminum, wood or plastic material (generally a stratified resin with glass fibers). The various parts of the prosthesis (socket, leg, foot) were joined by metal pieces. The foot was interchangeable and it was generally heavy, since it comprised a core of wood on the inside.

The development of new, light and resistant materials, such as thermosettable resins provided with carbon or aramid fiber, has prompted the Applicant to examine the possibility of producing prostheses for leg amputation which are much lighter than those of the prior art and which are no less comfortable for the user, in particular providing him with the necessary flexibility of use.

SUMMARY OF THE INVENTION

One object of the invention is, therefore, to provide a prosthesis for amputation of the leg which is lighter and easier to wear than those of the prior art and which, for the user, is just as practical to use as the ordinary endoskeletal prostheses.

The invention also has the object of providing a process for manufacturing such a prosthesis, which process is simple, easy to implement and relatively inexpensive.

To this end, to present invention provided a prosthesis for amputation of the leg, which comprises, in monobloc form:

- a socket of a thermosettable resin, preferably provided with reinforcement fibers;
- a hollow leg element rigidly integral with the socket, likewise of a thermosettable resin, preferably provided with reinforcement fibers;
- a hollow foot part rigidly integral with the leg element, and in which is lodged a rigid core of a foam of plastic or similar material, this foot part being likewise of a thermosettable resin, preferably provided with reinforcement fibers;
- a sole element of a thermosettable resin, preferably provided with reinforcement fibers, closing the hollow foot part at its base.

In a manner known per se, the prosthesis will additionally comprise, on the socket, on the leg element and on the foot part, a sheath of an expanded plastic material imitating flesh and, under the sole of thermosettable material, a heel element, a metatarsus element and an elastomer sole.

The essential characteristic of the invention thus lies in the fact that the socket, the leg element and the foot part are all hollow elements made of a light rigid material, such as a thermosettable material and, preferably, a thermosettable material provided with reinforcement fibers such as carbon fibers, aramid fibers or others.

The thermosettable material used will preferably be formed of a single layer.

A member for adjusting the height of the prosthesis may advantageously be provided below the rear part of the sole. It will consist, for example, of an element of plastic material screwed into a tapped hole in the part forming the sole. A part forming a cover may optionally be fitted into the height-adjusting element in order to hide it from view.

The leg prosthesis according to the invention may be made in a simple manner by means of a process comprising the following successive stages

- producing, from a cast of the stump, a socket of thermosettable material, preferably provided with reinforcement fibers;
- producing cores of easily destructible plastic material for shaping, respectively, the leg and foot parts of the prosthesis;
- maintaining the socket and the said cores in a position corresponding to that of the prosthesis and, if appropriate, placing in a detachable manner, under the core of the foot part, a sole element of thermosettable material, preferably provided with reinforcement fibers;
- producing, from the mold of the cores, a monobloc prosthesis of thermosettable material, preferably strengthened with reinforcement fibers, rigidly integral with the socket;
- withdrawing the core from the foot part and, if appropriate, from the sole element;
- destroying and removing, starting from the lower face, the leg core;
- repositioning the foot core and the sole element, and gluing the latter onto the foot part of the prosthesis.

These stages, which are characteristic of the process according to the invention, will be followed by stages known per se for positioning and fixing of the flexible metatarsus and heel elements, and of the sole of the prosthesis, and for ensheathing the prosthesis, thus made, in an expanded plastic material imitating flesh.

All these operations can be carried out in a simple manner by the skilled worker using ordinary materials, and, given the high mechanical resistance of thermosettable materials provided with carbon fibers, it is thus possible to produce, at a modest cost, a light prosthesis which is easy to wear and very resistant.

BRIEF DESCRIPTION OF THE INVENTION

The attached drawings, which are not limiting in nature, illustrate an embodiment of the prosthesis according to the invention and the process for it preparation. In these drawings:

FIG. 1 is a vertical section of the prosthesis, essentially following its median plane;

FIG. 2 is a section of the lower part of the prosthesis;

FIG. 3 is a partial cutaway view following the arrow F in FIG. 1;

FIGS. 4a and 4b are partial sections following the line IV—IV in FIG. 1 of two embodiments of the prosthesis;

FIGS. 5-7, 8a, 8b, and 9-11 are diagrammatic views illustrating the successive stages of the process for manufacturing the prosthesis.

DETAILED DESCRIPTION OF THE DRAWINGS

As can be seen in FIG. 1, the prosthesis according to the invention comprises a socket 1 intended to receive the leg stump, a hollow leg part 2 rigidly integral with the socket 1, and a hollow foot part 3 extending the leg part downward and closed at its lower part by a glued-on sole 4. The elements 1, 2, 3 and 4 are all of one and the same material, a thermosettable resin, preferably provided with carbon fibers, which combines an excellent mechanical resistance with considerable ease of shaping and an appreciable lightness. As can be seen, the leg part 2 and the foot part 3 constitute one and the same piece, and the element 2 is, as will be seen hereinafter, heat-sealed at manufacture against the socket 1. Lodged in the foot part 3 is a removable reinforcing element 26 of a foam of rigid plastic material.

Below the foot part 3 and the sole 4 there is glued an actual sole 5, of plastic material, with interposition, at the front, of a metatarsus element 6 and, at the rear, of a heel corner 7, both made of an elastomer, for example a polyurethane elastomer, designed to impart to the sole a sufficient flexibility.

A tapped recess 8 may be provided under the rear part of the sole 5 (FIG. 2), into which recess there is screwed a cylindrical and externally threaded height-adjusting element. A screen 11 may be fitted in a hollow part 10 in the base of this adjustment element 9, which screen 11 is intended to conceal the adjustment element and give it a foundation.

A layer of expanded plastic material 12 of expanded material of flesh color is provided on the leg part 2 and foot part 3 of the prosthesis, which layer extends as a thinner film over the socket 1.

The absence of any core of wood or another heavy material inside the foot part will be noticed, this being substituted by the light reinforcement element 26 of foam. The excellent mechanical resistance of the thermosettable material provided with carbon fibers and the process, which will be described hereinafter, permit the omission of this heavy reinforcing material and thus make it possible to considerably lighten the prosthesis.

As shown in FIG. 4a, the element 26 can be monobloc and bear by means of a flat surface on the sole 5, the metatarsus 6 and the heel element 7 in order to form a relatively rigid prosthesis which is suitable, for example, for an elderly person. Alternatively (FIG. 4b), the element 26 can comprise a rigid central part 26a and two lateral parts 26b of flexible foam and in the shape of a corner whose ridge is arranged following the median longitudinal part of the sole 5. The two parts 26b thus act, at the base of the prosthesis, as two real articulations capable of deforming laterally and of preventing or compensating for any awkward movement of the patient equipped with this prosthesis.

The stages of the process for manufacturing the latter will now be described successively with reference to the diagrammatic FIGS. 5 to 11.

As can be seen in FIG. 5, a plaster cast 20 is first made of the stump of the amputated limb, and a gauge 21 is used to roughly determine the dimensions and the height of the prosthesis to be produced, and an adapted socket 1, for example of carbon fiber laminate and plastic material, is tried on the plaster cast 20. This socket 1 can also be made, in a manner known per se, to the dimensions of the cast 20.

After this stage, which can be designated the testing stage, a leg core 25 and foot core 26 of a rigid expanded material are chosen, of a size appropriate to that of the prosthesis to be made. These elements can be assembled by fitting parts of complementary shape such as 30a and 30b (FIG. 6), and the upper part of the leg core is hollowed out matching the profile of the socket in order to receive the latter (FIG. 7).

Depending on whether it is desired to produce a rigid prosthesis or a flexible prosthesis, the core 26 will be monobloc and of a rigid material (FIG. 8a), or will comprise a rigid central part 26a with flexible corner-shaped elements 26b arranged symmetrically on its base (FIG. 8b) as explained hereinabove.

The socket 1 and the cores 25 and 26 are then placed in a convenient position and are ensheathed with two films 27 of an impermeable plastic material, such as polyvinylchloride or polyvinylamide, between which there is interposed a carbon fiber textile (FIG. 9). The inner film 27 is glued on the socket 1, and a hardening resin is poured in between the two films to produce the outline of the leg parts 2 and 3 of the prosthesis of carbon fiber laminate, which is cut to the desired dimensions.

The foot part 26 is then withdrawn, and a tool 28 is used to destroy the leg core 25 from the inside, removing the fragments as one proceeds (FIG. 10).

The leg portion and the foot portion of the prosthesis are then ensheathed with a layer 12 of plastic foam, for example of flesh color, in order to give the prosthesis the appearance of a leg (FIG. 9). The core 26 is put into position, the sole 4 of carbon fiber laminate is glued on, and the metatarsus 6, the heel corner 7 and the actual sole 5 are put into position (FIG. 11).

As has been indicated, all these operations are simple to carry out and do not involve the use of either complicated equipment or expensive materials. Thus, it is possible to produce, at a low cost, the prosthesis according to the invention, which still possesses an excellent resistance and is distinguished by its lightness and its ease of use.

I claim:

1. A prosthesis for amputation of the leg, which comprises, in monobloc form;
    a socket (1) of a thermosettable resin;
    a hollow leg element (2) rigidly integral with the socket, likewise of a thermosettable resin;
    a hollow foot part (3) rigidly integral with the leg element (2), and in which is lodged a rigid core (26) of a foamed material, this foot part being likewise of a thermosettable material, wherein the core (26) of the hollow foot part comprises two corner-shaped parts (26b) of a flexible material, each with a ridge arranged essentially longitudinally along the foot part;
    a sole element (4) of a thermosettable resin, closing the hollow foot part at its base; and
    below the sole element (4), a heel corner (7), a metatarsus (6) and an actual elastomer sole (5).

2. The prosthesis as claimed in claim 1, which comprises, an outer layer 12 of an expanded plastic material imitating flesh.

3. The prosthesis as claimed in claim 2, which comprises a height-adjusting member comprising a cylindrical and externally threaded element (9) which is screwed into a tapped recess (8) in the rear part of the sole (5).

4. The prosthesis as claimed in claim 3, wherein the base of the cylindrical element (9) comprises a recess (10) to receive, by fitting, a screen (11) of flexible plastic material.

5. The prosthesis as claimed in claim 1, wherein reinforcement fibers are provided in the thermosettable resin in each of said socket, said hollow leg element, said hollow foot part, and said sole element.

6. The prosthesis as claimed in claim 1, wherein said rigid core is formed of foamed plastic.

* * * * *